US012003926B2

(12) United States Patent
Silberzahn et al.

(10) Patent No.: US 12,003,926 B2
(45) Date of Patent: Jun. 4, 2024

(54) HEARING ASSIST SYSTEMS AND METHODS FOR DETECTING A PHYSIOLOGICAL ATTRIBUTE OF A USER

(71) Applicant: SONOVA AG, Staefa (CH)

(72) Inventors: Konstantin Silberzahn, Meilen (CH); Markus Mueller, Männedorf (CH); Natasha Thumm, Wetzikon (CH); Markus Leuthold, Stäfa (CH); Christian Frei, Staefa (CH)

(73) Assignee: Sonova AG, Staefa (CH)

( * ) Notice: Subject to any disclaimer, the term of this patent is extended or adjusted under 35 U.S.C. 154(b) by 169 days.

(21) Appl. No.: 17/763,499

(22) PCT Filed: Sep. 28, 2020

(86) PCT No.: PCT/IB2020/059065
§ 371 (c)(1),
(2) Date: Mar. 24, 2022

(87) PCT Pub. No.: WO2021/064556
PCT Pub. Date: Apr. 8, 2021

(65) Prior Publication Data
US 2022/0377476 A1 Nov. 24, 2022

Related U.S. Application Data

(62) Division of application No. 16/587,759, filed on Sep. 30, 2019, now Pat. No. 11,115,764.

(51) Int. Cl.
*H04R 25/00* (2006.01)
*A61B 5/00* (2006.01)
(Continued)

(52) U.S. Cl.
CPC ............. *H04R 25/609* (2019.05); *A61B 5/25* (2021.01); *A61B 5/291* (2021.01); *A61B 5/6815* (2013.01);
(Continued)

(58) Field of Classification Search
CPC ................ H04R 25/609; H04R 25/652; H04R 2225/021; H04R 2225/025
See application file for complete search history.

(56) References Cited

U.S. PATENT DOCUMENTS 6,454,718 B1 9/2002 Clift
8,204,786 B2 6/2012 Leboeuf et al.
(Continued)

FOREIGN PATENT DOCUMENTS

CN 102469950 5/2012
CN 106994012 8/2017
(Continued)

OTHER PUBLICATIONS

"International Search Report and Written Opinion received on Jan. 15, 2021 in International Application No. PCT/IB2020/059065."

*Primary Examiner* — Suhan Ni
(74) *Attorney, Agent, or Firm* — ALG Intellectual Property, LLC

(57) ABSTRACT

An exemplary hearing system that is configured to assist a user in hearing includes an in-the-ear (ITE) component configured to fit at least partially within an ear canal of the user while the hearing system is worn by the user, a first sensor electrode provided on a surface of the ITE component and configured to contact, while the hearing system is worn by the user, outer ear tissue of the user, and a second sensor electrode configured to be located, while the hearing system is worn by the user, at an entrance to or outside of the ear canal of the user. The first sensor electrode and the second
(Continued)

sensor electrode may be configured to be used to detect a physiological attribute of the user while the hearing system is worn by the user. Corresponding methods and systems are also disclosed.

15 Claims, 14 Drawing Sheets

(51) Int. Cl.
 *A61B 5/25* (2021.01)
 *A61B 5/291* (2021.01)
(52) U.S. Cl.
 CPC .......... *A61B 5/6817* (2013.01); *A61B 5/6826* (2013.01); *H04R 25/652* (2013.01); *H04R 2225/021* (2013.01); *H04R 2225/025* (2013.01)

(56) References Cited

U.S. PATENT DOCUMENTS

| | | | |
|---|---|---|---|
| 8,647,270 B2 | 2/2014 | Leboeuf et al. | |
| 8,737,667 B2 | 5/2014 | Oh et al. | |
| 9,408,552 B2 | 8/2016 | Kidmose et al. | |
| 9,743,197 B2 | 8/2017 | Petersen et al. | |
| 9,918,650 B2 | 3/2018 | Kilsgaard et al. | |
| 9,987,489 B2 | 6/2018 | Goodall et al. | |
| 10,575,106 B1 * | 2/2020 | Bergmann | H04R 25/505 |
| 2013/0206595 A1 | 8/2013 | Lee et al. | |
| 2015/0146899 A1 | 5/2015 | Dzarnoski et al. | |
| 2015/0256952 A1 | 9/2015 | Naumann | |
| 2016/0310028 A1 | 10/2016 | Kidmose et al. | |
| 2017/0238812 A1 | 8/2017 | Atlas | |
| 2017/0311097 A1 | 10/2017 | Nielsen | |
| 2017/0316192 A1 | 11/2017 | Razouane | |
| 2018/0014741 A1 | 1/2018 | Chou | |
| 2019/0111261 A1 | 4/2019 | Glenn | |
| 2019/0117155 A1 | 4/2019 | Cross et al. | |
| 2019/0132683 A1 * | 5/2019 | Sacha | H04R 25/556 |

FOREIGN PATENT DOCUMENTS

| | | |
|---|---|---|
| DE | 102006017970 | 10/2007 |
| EP | 3021599 | 5/2016 |
| EP | 3238616 | 11/2017 |
| EP | 3313092 | 4/2018 |
| EP | 3477968 | 5/2019 |
| WO | 2018103861 | 6/2018 |
| WO | 2018137662 | 8/2018 |
| WO | 2018186506 | 10/2018 |

\* cited by examiner

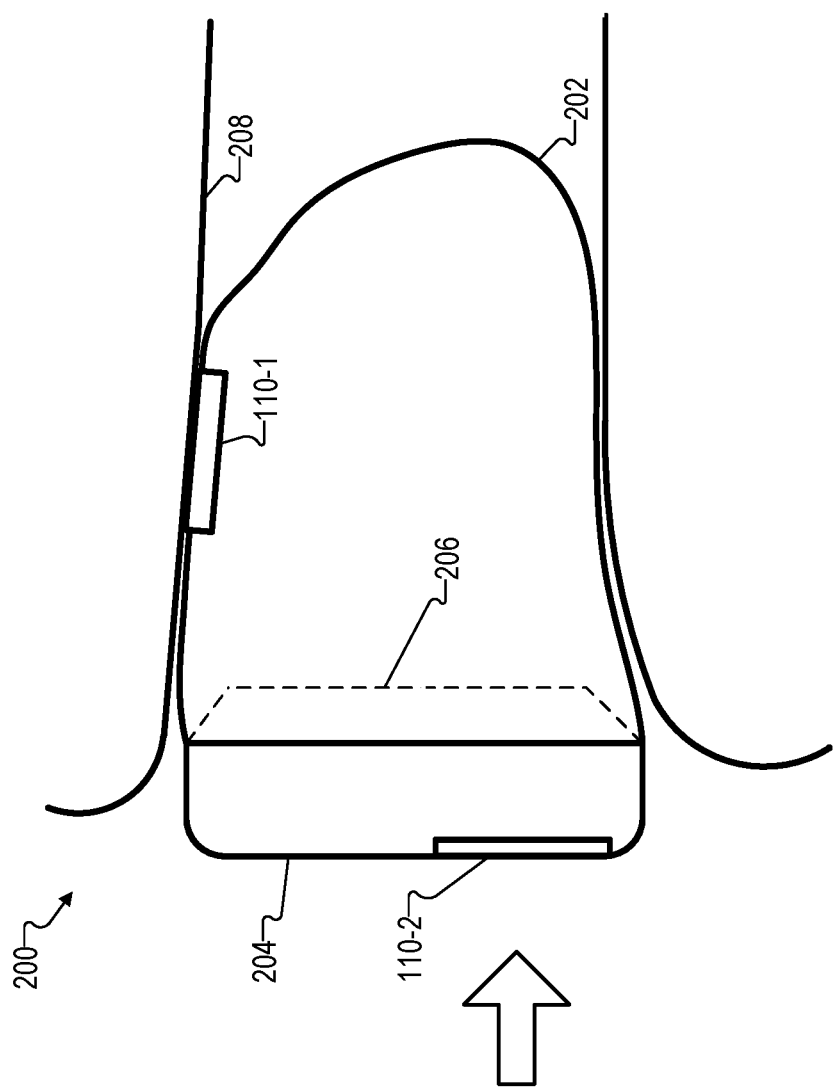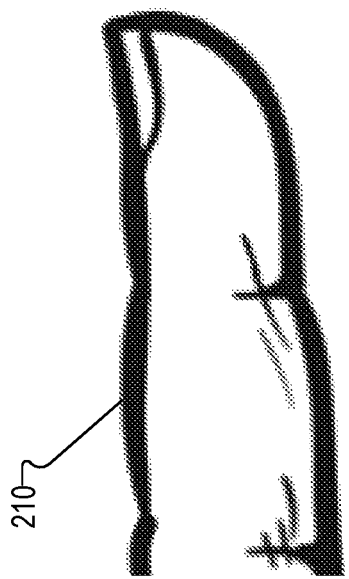
Fig. 2

HEARING ASSIST SYSTEMS AND METHODS FOR DETECTING A PHYSIOLOGICAL ATTRIBUTE OF A USER

RELATED APPLICATIONS

The present application claims priority to U.S. patent application Ser. No. 16/587,759, filed on Sep. 30, 2019, and entitled "Hearing Systems, Sensor Systems, and Methods for Detecting a Physiological Attribute of a User," the contents of which are hereby incorporated by reference in their entirety.

BACKGROUND INFORMATION

Hearing systems are used to improve the hearing capability and/or communication capability of users. Such hearing systems are configured to process a received input sound signal (e.g., ambient sound) and then provide the processed input sound signal to the user (e.g., through a hearing device such as a hearing aid). Hearing systems may use an in-the-ear ("ITE") component to facilitate providing the processed input sound signal to the user. Such ITE components are configured to fit at least partially within an ear canal of the user.

In addition to being used to facilitate providing the processed input sound signal to the user, such ITE components may also include electrodes that may be configured to contact outer ear tissue within the ear canal of the user while the ITE component is worn by the user. Such electrodes may be used, for example, to detect electrical activity associated with the user. However, there remains room for improvement in the configuration and/or functionality of such electrodes in the detection of the electrical activity associated with the user.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 2-12 illustrate various exemplary configurations of components that may be implemented as part of the hearing system shown in FIG. 1 according to principles described herein.

DETAILED DESCRIPTION

Hearing systems, sensor systems, and methods for detecting a physiological attribute of a user are described herein. As will be described in more detail below, an exemplary hearing system configured to assist a user in hearing may include an ITE component configured to fit at least partially within an ear canal of the user while the hearing system is worn by the user, a first sensor electrode provided on a surface of the ITE component and configured to contact, while the hearing system is worn by the user, outer ear tissue of the user, and a second sensor electrode configured to be located, while the hearing system is worn by the user, at an entrance to or outside of the ear canal of the user. The first sensor electrode and the second sensor electrode may be configured to be used to detect a physiological attribute of the user while the hearing system is worn by the user.

By providing a hearing system with sensor electrodes configured according to principles described herein, it is possible to efficiently and conveniently use the hearing system to detect one or more physiological attributes of a user. In addition, components (e.g. an ITE component, a behind-the-ear ("BTE") component, etc.) of a hearing system that have sensor electrodes such as those described herein may be easier to manufacture and/or more comfortable for a user to wear than conventional components of hearing systems. Other benefits of the hearing systems, sensor systems, and methods such as those described herein will be made apparent herein.

Figure 1:
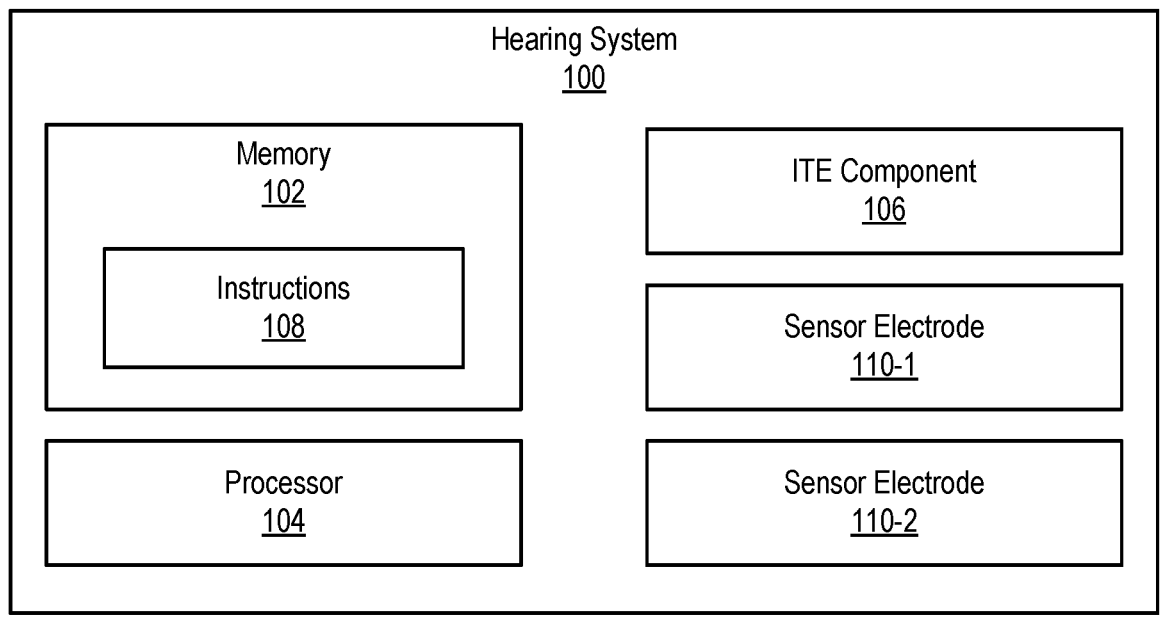
FIG. 1 illustrates an exemplary hearing system according to principles described herein.

FIG. 1 illustrates an exemplary hearing system 100 that is configured to assist a user in hearing. As shown, hearing system 100 may include, without limitation, a memory 102, a processor 104, an ITE component 106, and sensor electrodes 110 (e.g., sensor electrode 110-1 and 110-2) selectively and communicatively coupled to one another. Although FIG. 1 only shows two sensor electrodes 110, it is understood that any suitable number of sensor electrodes 110 may be provided as part of hearing system 100 as may serve a particular implementation. Memory 102 and processor 104 may each include or be implemented by hardware and/or software components (e.g., processors, memories, communication interfaces, instructions stored in memory for execution by the processors, etc.). In some examples, memory 102 and processor 104 may be housed within or form part of ITE component 106. In other examples, memory 102 and processor 104 may be located separately from ITE component 106 (e.g., in a BTE component). In some alternative examples, memory 102 and processor 104 may be distributed between multiple devices (e.g., multiple hearing devices in a binaural hearing system) and/or multiple locations as may serve a particular implementation.

Memory 102 may maintain (e.g., store) executable data used by processor 104 to perform any of the operations associated with hearing system 100 described herein. For example, memory 102 may store instructions 108 that may be executed by processor 104 to perform any of the operations associated with hearing system 100 described herein. Instructions 108 may be implemented by any suitable application, software, code, and/or other executable data instance.

Memory 102 may also maintain any data received, generated, managed, used, and/or transmitted by processor 104. For example, memory 102 may maintain any suitable data associated with physiological attributes of a user that may be detected using one or more sensor electrodes such as those described herein. As used herein, a "physiological attribute" may refer to any characteristic that may be associated with the functioning of the body of the user of hearing system 100. For example, a physiological attribute may comprise a hydration level within the ear canal of the user, brain activity indicated in an electroencephalogram ("EEG") measurement, a heartbeat attribute indicated in an electrocardiogram ("ECG") measurement, and/or any other suitable physiological attribute. Memory 102 may maintain additional or alternative data in other implementations.

Processor 104 is configured to perform any suitable processing operation that may be associated with hearing system 100. For example, when hearing system 100 is implemented by a hearing aid device, such processing operations may include monitoring ambient sound and/or representing sound to a user via an in-ear receiver. In examples where hearing system 100 is implemented as part of a cochlear implant system, such processing operations may include directing a cochlear implant to generate and apply electrical stimulation representative of one or more audio signals (e.g., one or more audio signals detected by a microphone, input by way of an auxiliary audio input port, etc.) to one or more stimulation sites associated with an auditory pathway (e.g., the auditory nerve) of a user. Processor 104 may be implemented by any suitable combination of hardware and software.

In addition, processor 104 is configured to perform any suitable processing operation associated with hearing system 100 using sensor electrodes 110 to detect one or more physiological attributes of a user. For example, processor 104 may control operation of sensor electrodes in any suitable manner to detect a physiological attribute of a user.

Hearing system (e.g., processor 104) may perform an operation to detect a physiological attribute of a user at any suitable time. For example, hearing system 100 may use sensor electrodes 110 to periodically, randomly, or continually detect a physiological attribute of the user. To illustrate, in implementations where sensor electrodes 110 are configured to be used to take an EEG measurement of the user, hearing system 100 may use sensor electrodes 110 to take the EEG measurement each time hearing system 100 is turned on while worn by the user, Additionally or alternatively, hearing system 100 may use sensor electrodes 110 to detect a physiological attribute at a particular time each hour, at a particular time each day, etc. Additionally or alternatively, hearing system 100 may use sensor electrodes 110 to detect the physiological attribute in response to an occurrence of a predefined event. For example, if no physical movement is detected from the user for a predefined amount of time (e.g., 10 minutes), hearing system 100 may use sensor electrodes 110 to detect the physiological attribute of the user based on the lack of physical movement.

Hearing system 100 may perform any suitable action associated with information obtained while detecting a physiological attribute of the user. For example, hearing system 100 may direct memory 102 to store the information obtained while detecting the physiological attribute. In certain examples, hearing system 100 may direct a communication interface of hearing system 100 to transmit the information in any suitable manner and at any suitable time to one or more external devices (e.g., a smartphone, a tablet computer, a fitting system, etc.) communicatively coupled to hearing system for processing and/or analysis.

Sensor electrodes 110 are configured facilitate hearing system 100 detecting a physiological attribute of the user while hearing system 100 is worn by the user. Sensor electrodes 110 may be arranged in any suitable manner to facilitate detection of a physiological attribute.

For example, sensor electrode 110-1 may be configured to be provided on a surface of ITE component 106 and may be configured to contact outer ear tissue of the user while hearing system 100 is worn by the user. As used herein, "outer ear tissue" refers to any tissue of the ear that is either inside the ear canal or that is outside of the ear canal. For example, any portion (e.g., the helix, the concha, etc.) of the pinna of the ear may be considered as outer ear tissue for the purposes of this disclosure. Exemplary configurations of sensor 110-1 will be described herein in connection with the figures.

On the other hand, sensor electrode 110-2 may be configured to be located at an entrance to or outside of the ear canal of the user while hearing system 100 is worn by the user. In certain examples, sensor electrode 110-2 may be located on a surface of ITE component 106 that is at the entrance to or outside of the ear canal. In certain alternative implementations, sensor electrode 110-2 may be provided on an additional component of hearing system 100 that is communicatively coupled to ITE component 106. For example, sensor electrode 110-2 may be provided on any suitable surface of a behind-the-ear ("BTE") component of hearing system 100. Exemplary configurations of sensor 110-2 will be described herein in connection with the figures.

Sensor electrodes 110 may be manufactured in any suitable manner. In certain examples, one or more of sensor electrodes 110 may be provided in a through hole provided in a component (e.g., ITE component 106) of hearing system 100 and may be electrically connected to circuitry and/or other electronics by way of one or more wires provided through the through hole. Alternatively, one or more of sensor electrodes 110 may be surface electrodes that are provided on an outer surface of a component of hearing system 100. In such examples, one or more of sensors 110 may be manufactured through a laser direct structuring ("LDS") process, an aerosol jet printing ("AJP") process, a ProtoPaint LDS process, and/or any other suitable process.

Sensor electrodes 110 may be formed of any suitable metal, combination of metals, or conductive non-metallic materials. For example, sensor electrodes 110 may be formed of copper, nickel, gold, a conductive elastomer (e.g., conductive silicone rubber), and/or any other suitable conductive material.

In certain examples, sensor electrodes 110 may be coated with a protective coating to improve corrosion resistance. For example, a P2i coating may be used on one or more of sensor electrodes 110 in certain examples.

Sensor electrodes 110 may be electrically connected to circuitry and/or other electronics (e.g., within a BTE component and/or with a shell of ITE component 106) associated with hearing system 100 in any suitable manner. For example, sensor electrodes 110 may be electrically connected to such circuitry and/or other electronics by way of a wire, a flexible printed circuit board, or a conductive path, which may be formed through an LDS process, an AJP process, or any other suitable process. In certain examples, the electrical connection between sensor electrodes 110 and the circuitry and/or other electronics may be facilitated by soldering, a spring, conductive glue, and/or any other suitable manner. In examples where a conductive path is used, such a conductive path may be coated by a protective coating (e.g., an acrylic lacquer) to prevent corrosion and/or unwanted measurements.

Sensor electrodes 110 may have any suitable, configuration, size, and/or shape as may serve a particular implementation. For example, sensor electrodes 110 may be shaped as a square, a rectangle, a circle, etc. In certain examples, one or more of sensor electrodes 110 may have a specific layout configured to facilitate detecting a particular type of physiological attribute of the user. For example, sensor electrode 110-1 may include a plurality of parallel electrode strips configured to create an electromagnetic field that may be used to determine skin capacitance of the user within the user's ear canal. In other examples, sensor electrode 110-2 may be specifically configured to contact, for example, a finger of the user to facilitate taking an ECG measurement of the user.

ITE component 106 is configured to fit at least partially within an ear canal of a user while hearing system 100 is worn by the user. Any suitable type of ITE component may be used for ITE component 106 as may serve a particular implementation. For example, in certain implementations, ITE component 106 may include a shell that is configured to at least partially inserted within the ear canal of a user. In certain examples, sensor electrode 110-1 may be provided on an outer surface of the shell. With such a configuration, sensor electrode 110-1 may be configured to contact a wall of the ear canal of the user when ITE component 106 is inserted within the ear canal of the user.

The shell of ITE component 106 may correspond to any suitable type of shell that may be used as part of ITE component 106. For example, in certain implementations the shell may have a contoured outer shape that is custom made for a particular user. Alternatively, the shell may have a standard shape that is configured to fit at least partially within the ear canal of any one of a plurality of users.

The shell of ITE component 106 may be formed of any suitable material as may serve a particular implementation. For example, the shell may be metallic or non-metallic in certain implementations. A non-metallic shell may be formed of any one or a combination materials such as Nylon, acrylonitrile butadiene styrene ("ABS"), polycarbonate ("PC"), polyphenylene sulfide ("PPS"), polyetheretherketone ("PEEK"), liquid crystal polymer, conductive silicone, acrylates, and/or any other suitable non-metallic material. A metallic shell may be formed, for example, of titanium or any other suitable metal.

In examples where a conductive shell is used, the entire outer surface of the shell may implement or form sensor electrode 110-1. For example, the shell may be formed of conductive silicone, titanium, or any other suitable conductive material such that the entire outer surface of the shell functions as sensor electrode 110-1. With such a configuration, it may be possible to ensure that there is good contact between sensor electrode 110-1 and outer ear tissue within the ear canal of the user.

The shell may be manufactured using any suitable manufacturing process as may serve a particular implementation. In certain examples, a three-dimensional ("3D") printing process may be used to customize the shell to fit a particular user. By using a 3D printing process to manufacture a custom shell for a particular user, it is possible to reduce costs associated with manufacturing a custom shell as compared with other manufacturing methods such as injection molding. However, in certain alternative implementations, an injection molding process may be used to manufacture a shell.

In certain examples, the shell may be a molded interconnect device ("MID") shell. MIDs are circuits that are directly integrated into the shape of a polymer component. A MID shell may be manufactured in any suitable manner. For example, a MID shell may be manufactured using a 3D printing process in which 3D printable filaments are impregnated with an LDS additive that is configured to facilitate forming sensor electrode 110-1 and a conductive path on an outer surface of the shell during an LDS process. Any suitable LDS additive may be used as may serve a particular implementation. For example, an LDS additive may include a metal oxide (e.g., tin oxide), an organometallic complex (e.g., a palladium/palladium-containing heavy metal complex), and/or any other suitable material.

In certain examples, the shell of ITE component 106 may be configured to attach to a faceplate. In such examples, the shell may include an opening that is configured to receive the faceplate to close the shell at a side oriented towards the exterior of the user's ear. The opening of the shell may have any suitable size and/or shape as may serve a particular implementation. In certain examples, the opening of the shell may have a standard size that is the same regardless of the particular shape of the ear canal of the user. In other implementations, the opening may have a custom shape that may be different for each particular user depending on the contoured outer shape of the shell.

The faceplate is configured to fit within the opening provided in the shell and face out of the ear canal of the user when the shell is inserted into the ear canal of the user. The faceplate may be formed of any suitable material. For example, the faceplate may be formed of the same material as the shell (e.g., Nylon, ABS, PC, PPS, PEEK, liquid crystal polymer, etc.) or a different material.

The faceplate may be manufactured in any suitable manner. For example, in certain implementations, the faceplate may be 3D printed. Alternatively, the faceplate may be manufactured using an injection molding process.

The faceplate may have any suitable configuration as may serve a particular implementation. For example, in certain implementations, the faceplate may have a standard shape that is configured to fit within a standard opening provided in the shell. In such examples, the faceplate may be formed by using an injection molding process. In certain alternative implementations, the faceplate may be custom made to fit the contoured outer shape of the shell. In such implementations, a 3D printing process may be used to manufacture the faceplate.

In certain examples, the faceplate may include one or more elements that facilitate detection of a physiological attribute of the user and operation and/or manual adjustment of hearing system 100. For example, the faceplate may include a push button (e.g., that may be used to change hearing aid programs), a volume adjustment dial, a battery door usable to access a battery housed within the shell, and/or any other suitable element. Additionally or alternatively, the faceplate may include one or more microphones, a vent to aid in the reduction of occlusion, a removal handle, and/or any other suitable feature.

In certain implementations, sensor electrode 110-2 may be provided on a surface of the faceplate that faces away from the user. When implemented in such a manner, sensor electrode 110-2 may be configured to be touched by a finger of the user during detection of the physiological attribute. In such examples, sensor electrode 110-2 may be located on any suitable portion of the faceplate. For example, sensor electrode 110-2 may be included as part of the push button or part of the battery door on the faceplate in certain implementations.

ITE component 106 may have any other suitable components as may serve a particular implementation. For example, in certain implementations, ITE component 106 may include a microphone configured to detect an audio signal. Additionally or alternatively, ITE component 106 may include a receiver (e.g., a speaker) configured to deliver an audio signal to the user.

FIG. 2 shows an exemplary configuration 200 of ITE component 106. As shown in FIG. 2, ITE component 106 includes a shell 202, a faceplate 204, sensor electrode 110-1, and sensor electrode 110-2, each of which may be implemented as described above. As shown in FIG. 2, faceplate 204 is configured to fit within an opening 206 of shell 202. In the example shown in FIG. 2, opening 206 of shell 202 is indicated by dashed lines and opens to the left to receive faceplate 204 and close shell 202 at a side oriented towards the exterior of the user's ear.

As shown in FIG. 2, sensor electrode 110-1 is provided on an outer surface of shell 200 such that sensor electrode 110-1 is configured to directly contact a wall of ear canal 208 of the user while ITE component 106 is worn by the user. Sensor 110-2 on the other hand is provided on a surface of faceplate 202 in the example shown in FIG. 2 and is configured to be touched by a finger 210 of the user during measurement of the physiological attribute. For example, while ITE component 106 is within ear canal 208, the user may move finger 210 in the direction of the arrow to touch sensor electrode 110-2 with finger 210. In so doing, sensor electrodes 110 would be in contact with two parts of the user's body to form a measurement loop through or close by the heart of the user. While finger 210 touches sensor electrode 110-2 and sensor electrode 110-1 touches the wall within ear canal 208, hearing system 100 may take an ECG measurement based on electrical activity associated with the user detected through sensor electrodes 110-1 and 110-2.

In the example shown in FIG. 2, circuitry and/or any other suitable electronics (not shown) may be provided within shell 202. Sensor electrodes 110-1 and 110-2 may be electrically connected to the circuitry and/or other electronics within shell 202 in any suitable manner, such as described herein. For example, sensor electrode 110-1 may be connected to one or more wires that go through a through hole provided in shell 202. In such examples, sensor electrode 110-1 may be fixed within the through hole by using glue, any suitable mechanical retention mechanism, and/or a spring. Alternatively, sensor electrode 110-1 may be conductively connected to a conductive path (e.g., an LDS formed conductive path, an AJP formed conductive path, etc.) provided on an outer surface of shell 202. In such examples, sensor electrode 110-1 and the conductive path may be formed such that they follow the contoured outer surface of shell 202. This is beneficial in that it results in ITE component 106 being more comfortable to wear than conventional ITE components.

Although only one sensor electrode 110-1 is shown in FIG. 2, it is understood that any suitable number of sensor electrodes may be provided on the outer surface of shell 202 as may serve a particular implementation.

In certain examples, sensor electrode 110-1 may protrude from the outer surface of shell 202, as shown in FIG. 2. In certain alternative examples, sensor electrode 110-1 may be flush with the outer surface of shell 202.

Figure 3:
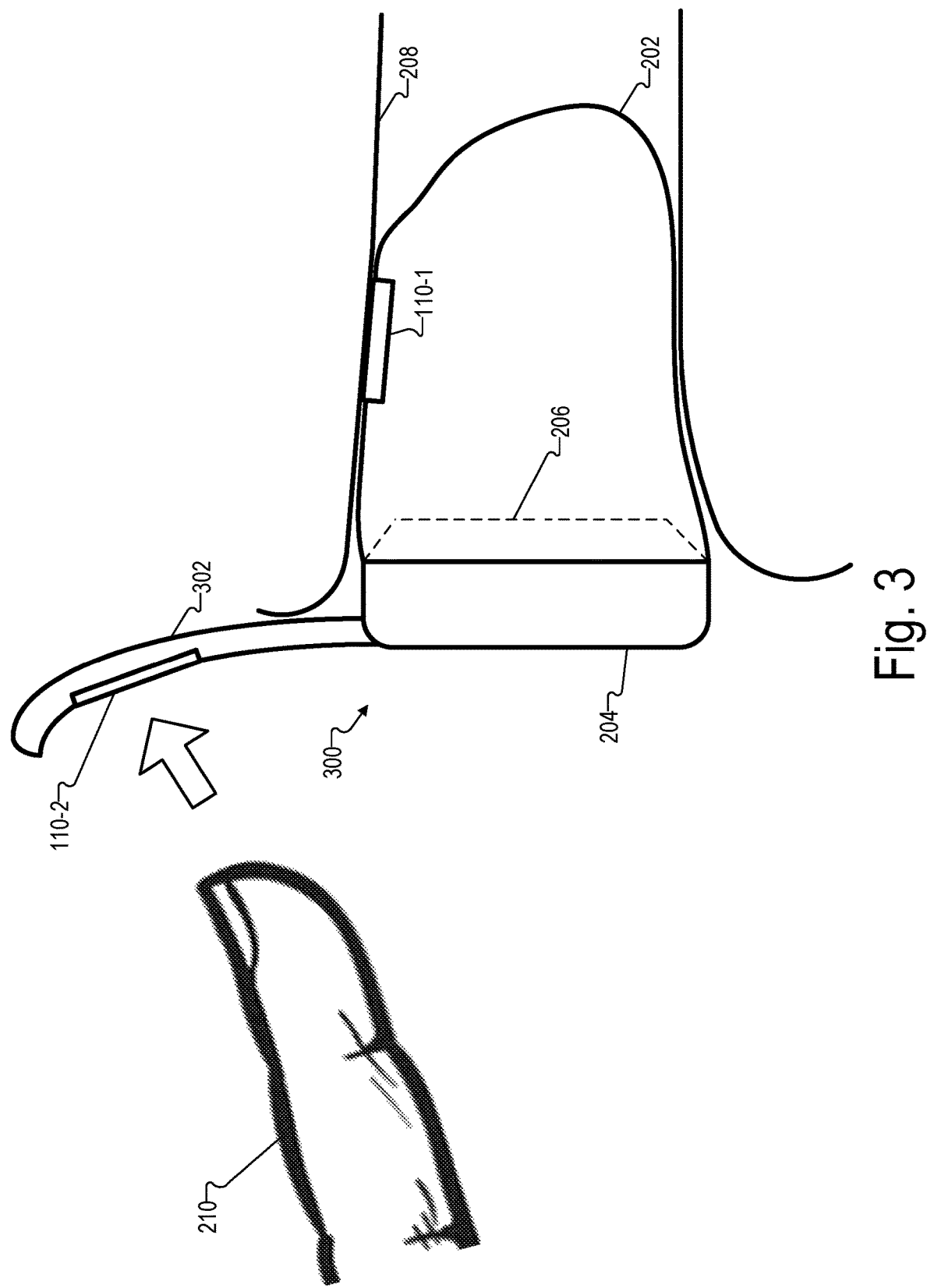

In certain examples, sensor electrode 110-2 may be provided on a retention member that is attached to ITE component 106. Such a retention member may be configured to be positioned within a concha of an ear of a user while hearing system 100 is worn by the user. To illustrate, FIG. 3 shows an exemplary configuration 300 of ITE component 106 in which a retention member 302 is attached to faceplate 202. In certain alternative examples, retention member 302 may be attached to or form part of shell 202. Retention member 302 is configured to retain ITE component 106 in position while ITE component 106 is worn by the user. As shown in the example in FIG. 3, sensor electrode 110-2 is provided on a surface of retention member 302 that faces away from the user. As such, in FIG. 3, sensor electrode 110-2 is configured to be contacted by finger 210 of the user while sensor electrode 110-1 and sensor electrode 110-2 are used by hearing system 100 to detect a physiological attribute of the user.

In the example shown in FIG. 3, sensor electrode 110-2 is electrically connected to circuitry and/or other electronics (not shown) within shell 202. In certain examples, sensor electrode 110-2 may be electrically connected to the circuitry and/or other electronics by way of one or more wires provided within retention member 302. Alternatively, sensor electrode 110-2 may be electrically connected to the circuitry and/or other electronics by way of a conductive path (e.g., an LDS formed conductive path, an AJP formed conductive path, etc.) that extends along an outer surface of retention member 302.

In certain examples, hearing system 100 may further include a BTE component that is communicatively coupled to ITE component 106. Such a BTE component is configured to be worn behind an ear of a user and may include circuitry (e.g., a processor similar to processor 104) configured to control operation of sensor electrodes 110. In such examples, ITE component 106 may further include a receiver (e.g., a speaker) configured to acoustically deliver an audio signal to the user as directed by the BTE component.

Figure 4:
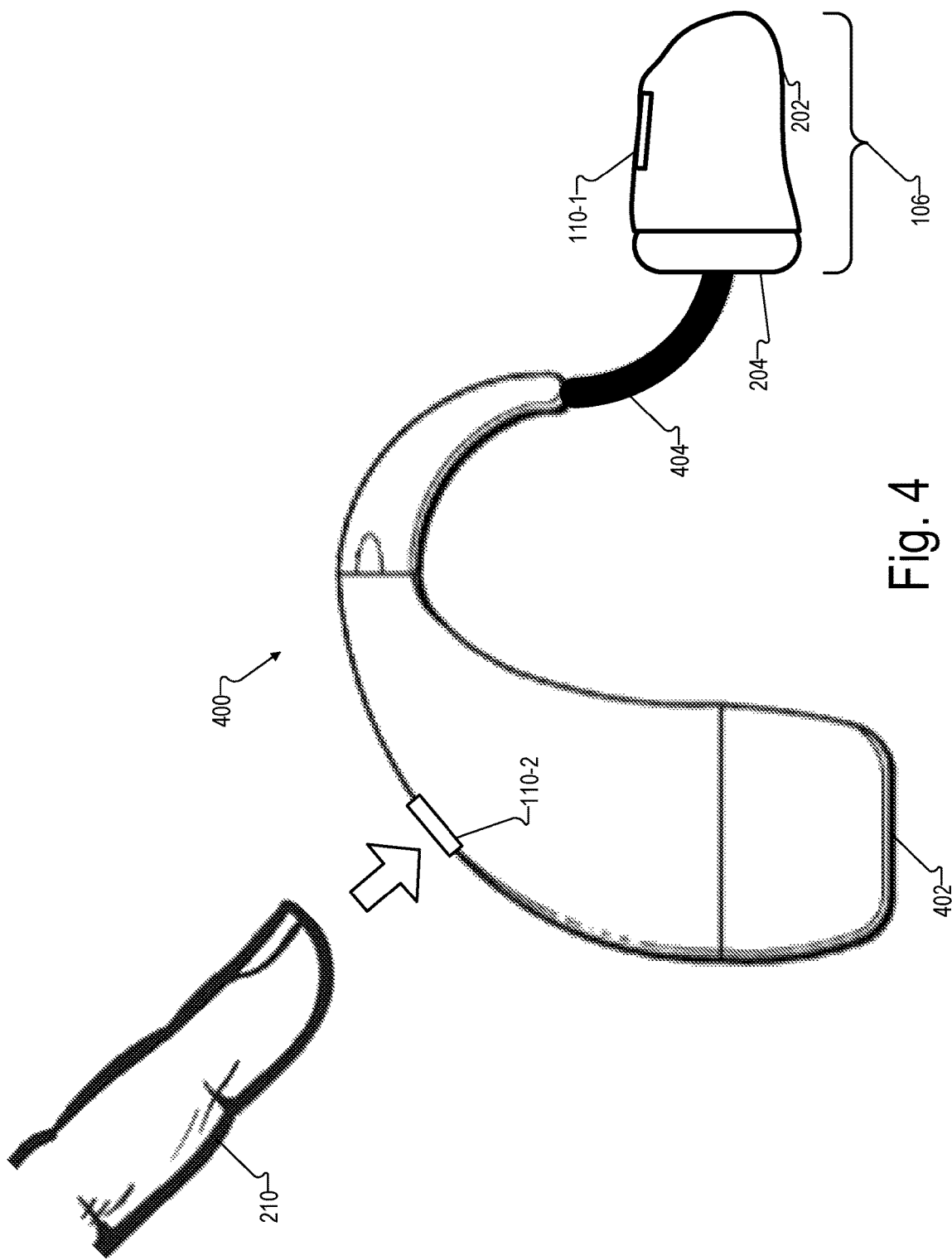

In certain examples, sensor electrode 110-2 may be provided on an outer surface of a BTE component. To illustrate, FIG. 4 shows an exemplary configuration 400 in which ITE component 106 is connected to a BTE component 402 by way of a connector portion 404, which may be implemented by any suitable wired connection. In the example shown in FIG. 4, sensor electrode 110-2 is provided on an outer surface of BTE component 402 and is configured to be contacted by finger 210 of the user while sensor electrode 110-1 and sensor electrode 110-2 are used to detect a physiological attribute of the user. Sensor electrode 110-1 may be electrically connected to circuitry within BTE component 402 in any suitable manner. For example, sensor electrode 110-1 may electrically connect to the circuitry within BTE component 402 by way of one or more wires (not shown) that extend within connector portion 404 from faceplate 204 to BTE component 402.

Figure 5:
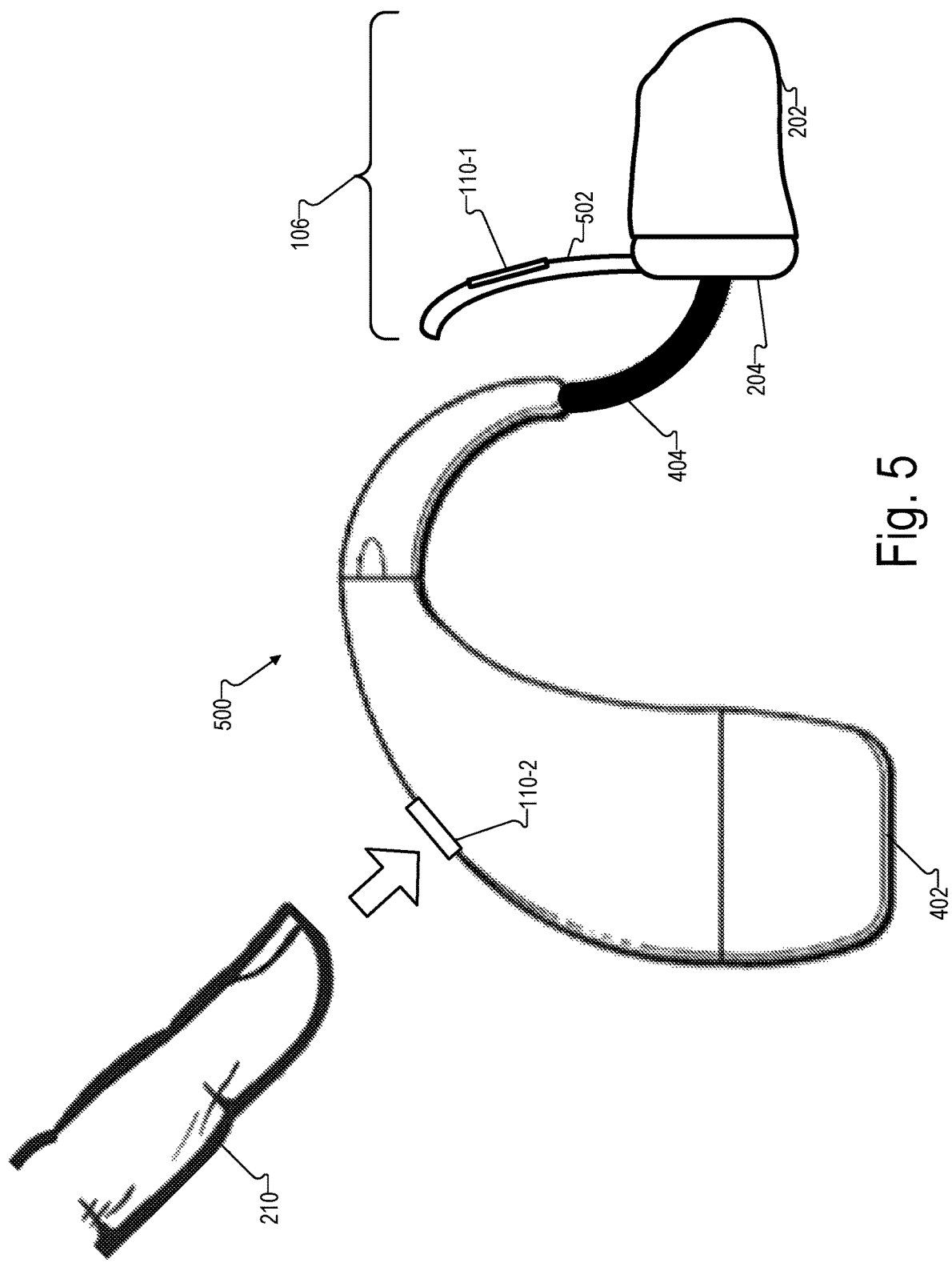

In certain examples, sensor electrode 110-1 may be provided on a retention member that is configured to contact outer ear tissue outside of the ear canal when ITE component is worn by the user. To illustrate, FIG. 5 shows an exemplary configuration 500 in which a retention member 502 is attached to faceplate 204 of ITE component 106. In the example shown in FIG. 5, sensor electrode 110-1 is configured to face towards and contact the outer ear tissue (e.g., the concha) of the user while ITE component 106 is worn by the user. FIG. 5 also shows sensor electrode 110-2 as being provided on an outer surface of BTE component 402. Similar to the example shown in FIG. 4, sensor electrode 110-2 is configured to be contacted by finger 210 of the user while sensor electrode 110-1 and sensor electrode 110-2 are used to detect a physiological attribute of the user.

In the example shown in FIG. 5, sensor electrode 110-1 is configured to electrically connect with circuitry and/or other electronics within shell 202 and/or within BTE component 402 in any suitable manner, such as described herein. In addition, sensor electrode 110-2 is configured to electrically connect with such circuitry and/or other electronics in any suitable manner. For example, sensor electrode 110-2 may electrically connect to circuitry provided within BTE component 402 by way of one or more wires provided through a through hole in a casing of BTE component 402.

Figure 6:
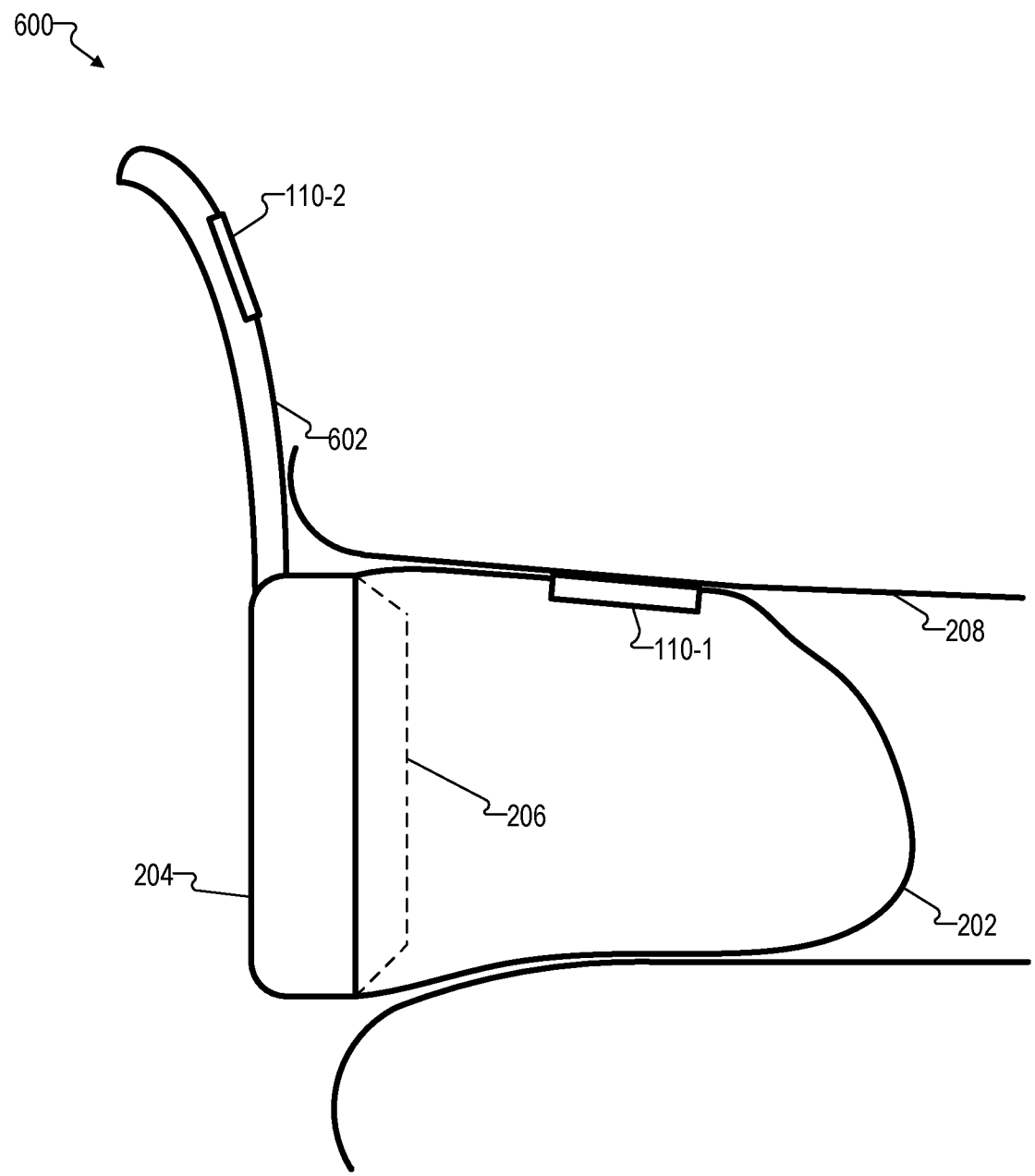

In certain implementations, sensor electrode 110-2 may be provided on a retention member that is configured to contact outer ear tissue outside of the ear canal while ITE component 106 is worn by the user. To illustrate, FIG. 6 shows an exemplary configuration 600 in which a retention member 602 is attached to faceplate 204 of ITE component 106. In the example shown in FIG. 6, sensor electrode 110-1 is configured to face towards and contact outer ear tissue (e.g., the concha) of the user while ITE component 106 is worn by the user. As such, in configuration 600, sensor electrode 110-2 is not configured to contact a finger of the user. In configuration 600 shown in FIG. 6, sensor electrodes 110 may be used, for example, to detect brain activity of the user through an EEG measurement. Configuration 600 may be used in certain examples where ITE component 106 is not communicatively connected to a BTE component (e.g., BTE component 402), as shown in FIG. 6. Alternatively, configuration 600 may be used in certain examples where ITE component 106 is communicatively connected to a BTE component.

Figure 7:
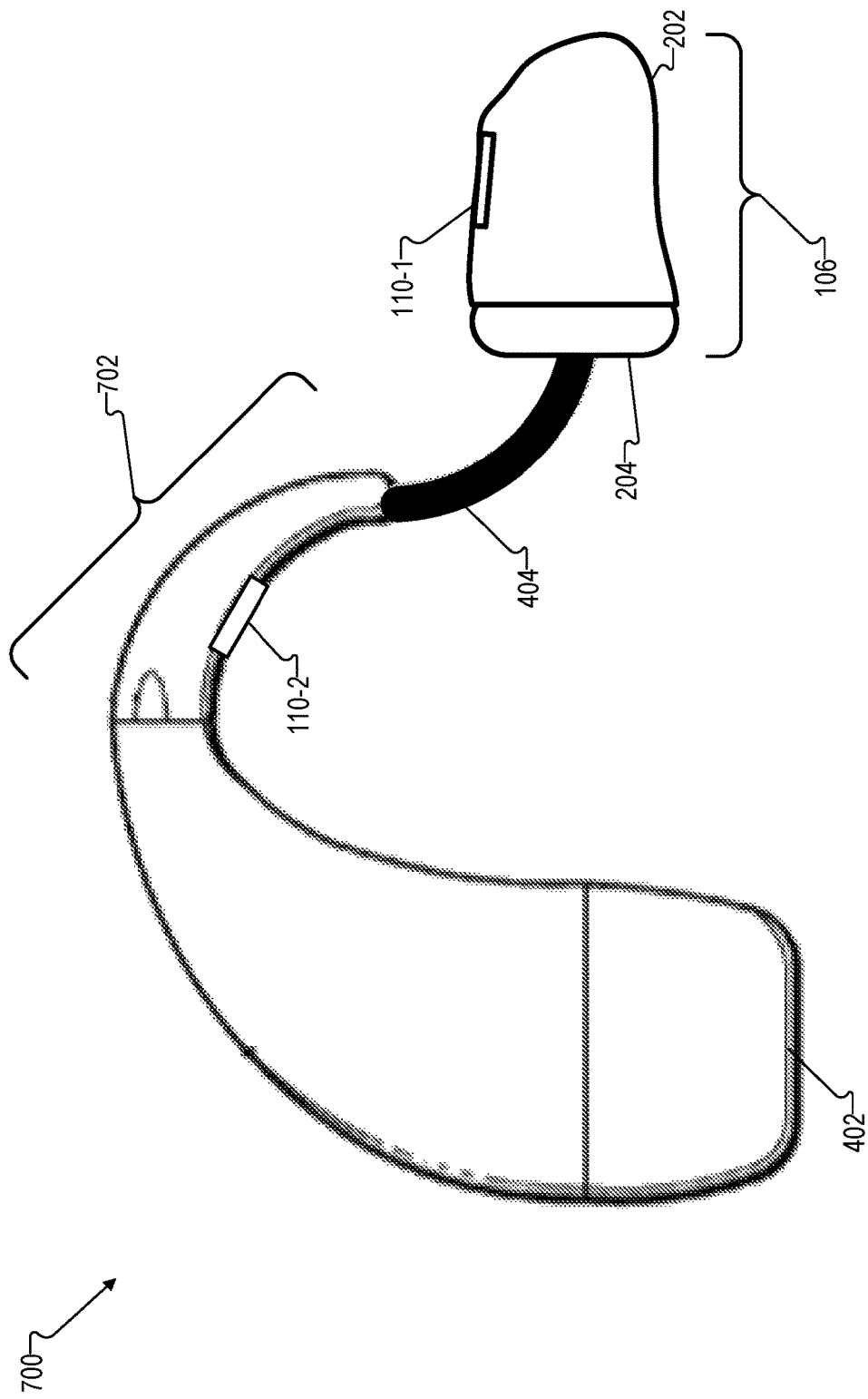

In certain examples, sensor electrode 110-2 may be configured to contact tissue of a user at a position that is outside of the ear canal while hearing system 100 is worn by the user. To illustrate, FIG. 7 shows an exemplary configuration 700 in which BTE component 402 includes a hook portion 702 configured to contact an upper portion of an ear of the user while BTE component 402 is worn behind the ear of the user. In configuration 700 shown in FIG. 7, sensor electrode 110-2 is provided on an outer surface of hook portion 702 so as to face downward when BTE component 402 is worn by the user. As such, in configuration 700 shown in FIG. 7, sensor electrode 110-2 is configured to contact the outer ear tissue of the user at the upper portion of the ear when BTE component 402 is worn by the user.

Sensor electrode 110-2 may be provided at other locations on an outer surface of BTE component 402 in other implementations. For example, instead of sensor electrode 110-2 being provided on an outer surface of hook portion 702, sensor electrode 110-2 may be provided on a portion of BTE component 402 that is configured to contact a rear portion of the ear of the user while hearing system 100 is worn by the user. Alternatively, sensor electrode 110-2 may be provided on a side surface of BTE component 402 that faces the skull of the user. In such examples, sensor electrode 110-2 may be configured to contact tissue covering the skull of the user while hearing system 100 is worn by the user.

Configuration 700 shows sensor electrode 110-2 as being a discrete sensor electrode provided on the outer surface of hook portion 702. However, it is understood that in certain alternative implementations hook portion 702 may be formed of a conductive material such that any portion of the outer surface of hook portion 702 may function as sensor electrode 110-2 for the purposes of detecting a physiological attribute of the user.

Figure 8:
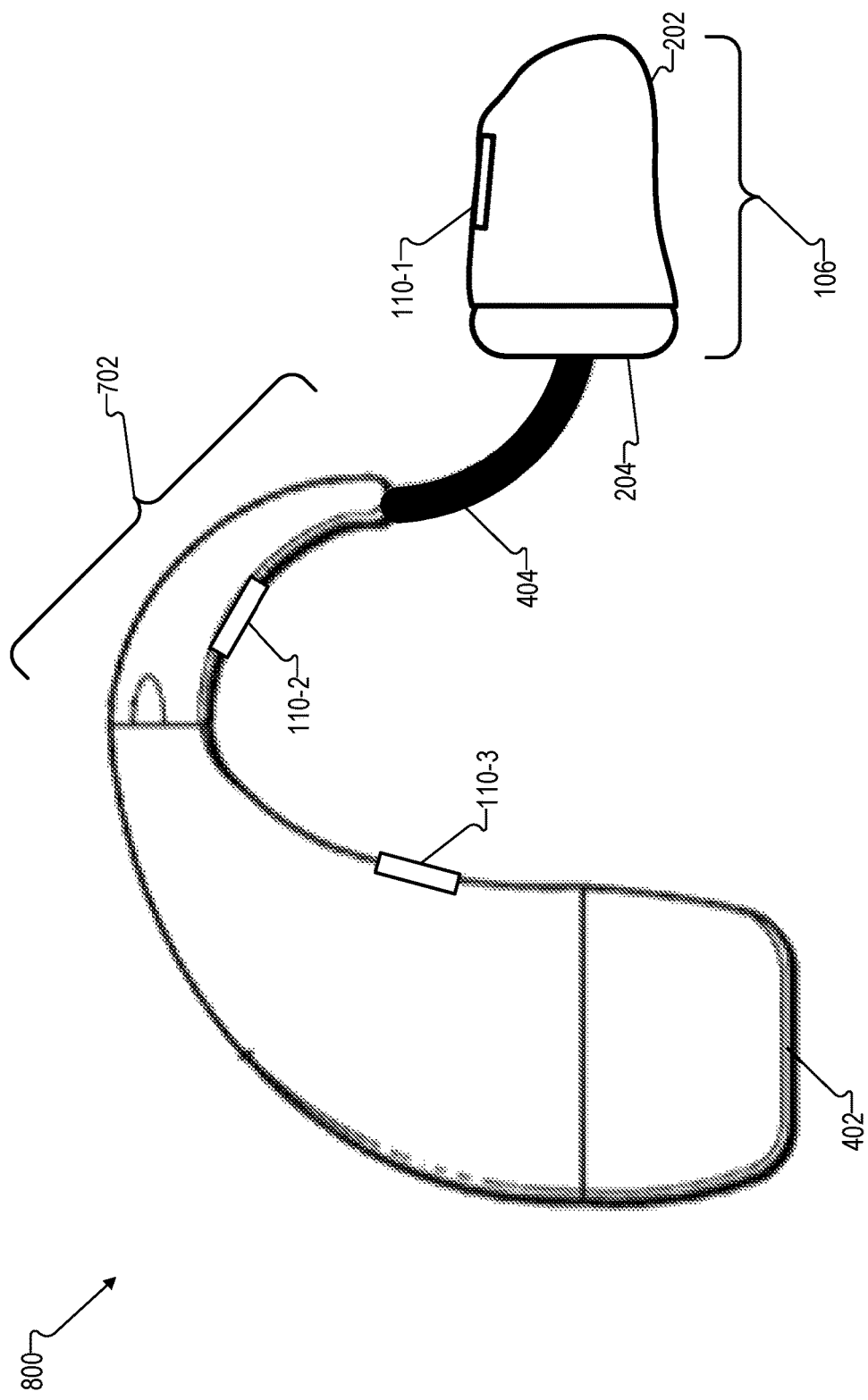

Although configuration 700 only shows one sensor electrode 110 provided on an outer surface of BTE component 402, it is understood that any suitable number of sensor electrodes 110 may be provided on an outer surface of BTE component 402 as may serve a particular implementation. To illustrate, FIG. 8 shows an exemplary configuration 800 in which an additional sensor electrode 110-3 is provided on BTE component 402 in addition to sensor electrode 110-2 provided on an outer surface of hook portion 702. As shown in FIG. 8, sensor electrode 110-3 is positioned so as to contact a rear portion of the ear of the user while hearing system 100 is worn by the user.

With a configuration such as configuration 800, hearing system 100 may use sensor electrodes 110-2 and 110-3 in any suitable manner to facilitate detecting a physiological attribute of the user. For example, hearing system 100 may use both sensor electrodes 110-2 and 110-3 concurrently to detect the physiological attribute of the user. Alternatively, hearing system 100 may monitor electrical signals detected by way of sensor electrodes 110-2 and 110-3 and select which of sensors 110-2 and 110-3 to use to detect the physiological attribute depending on which one of sensor electrodes 110-2 and 110-3 provides the best electrical signal.

Figure 9:
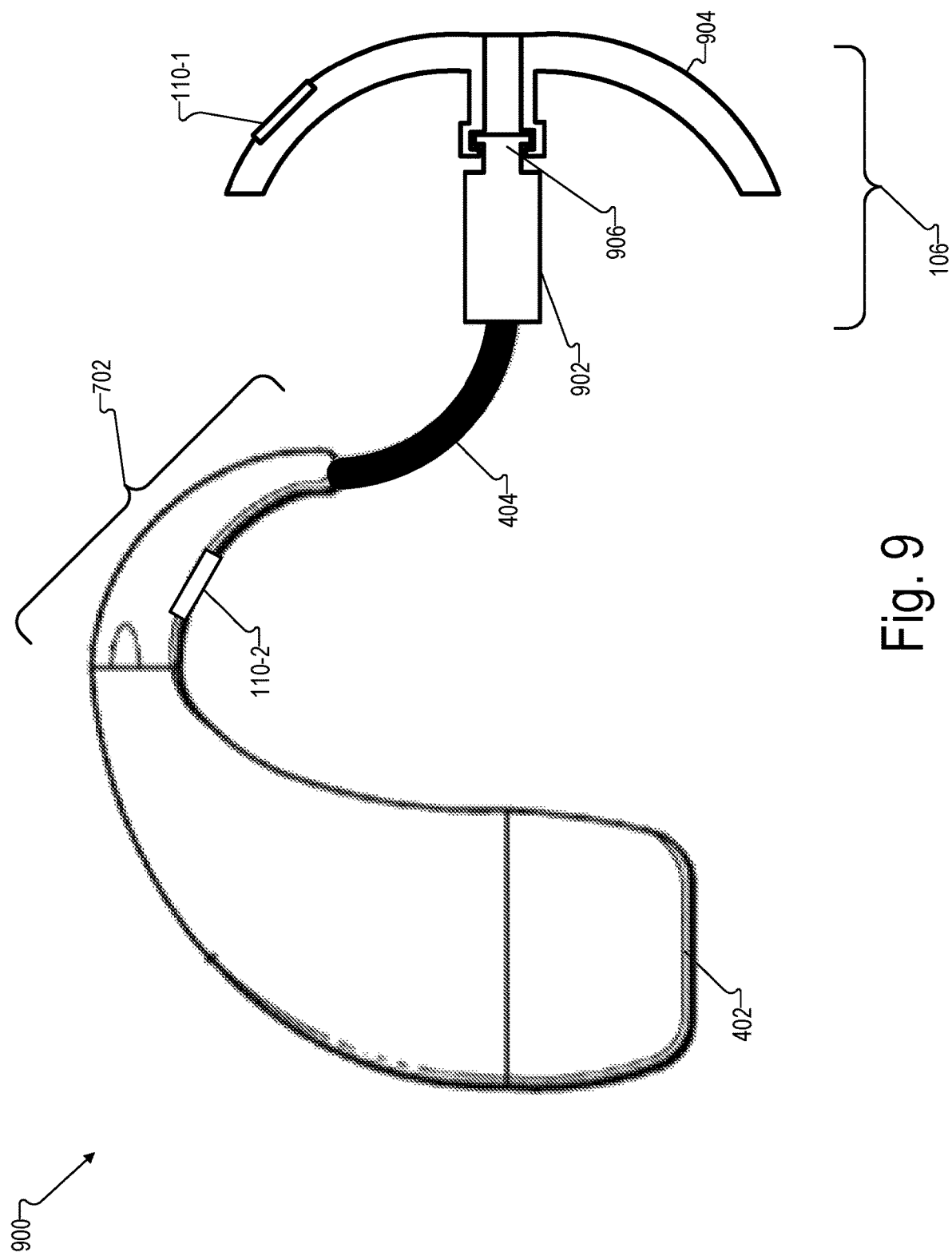

FIG. 9 shows an exemplary configuration 900 that is similar to configuration 700 shown in FIG. 7 except that ITE component 106 is configured differently. In particular, in the example shown in FIG. 9, BTE component 402 is attached by way of connector portion 404 to a receiver 902 instead of a faceplate (e.g., faceplate 204). Receiver 902 is connected to a shell 904 that has a dome shape and is configured to be flexible so as to bend when shell 904 is inserted within the ear canal of the user. In the example shown in FIG. 9, shell 904 includes sensor electrode 110-1 provided on an outer surface thereof at a position where sensor electrode 110-1 would contact outer ear tissue of the user when inserted in the ear canal.

In the example shown in FIG. 9, sensor electrode 110-1 may be electrically connected to receiver 902 in any suitable manner. For example, in FIG. 9, receiver 902 includes a conductive spout 906 configured to engage with shell 904. Conductive spout 906 may be metalized (e.g., through an LDS process) or may be formed of any suitable metal (e.g., stainless steel) or combination of metals. In certain examples, conductive spout 906 may be configured to contact a wire that extends from sensor electrode 110-1 to conductive spout 906 within shell 904. Alternatively, conductive spout 906 may be configured to contact a conductive path (e.g., an LDS formed conductive path) that extends from sensor electrode 110-1 to the conductive spout 906 and is provided on an outer surface of shell 904.

In certain examples, conductive spout 906 may be treated to improve corrosion resistance and/or conductivity. For example, conductive spout 906 may be plated in any suitable manner with gold and/or any other suitable metal in certain implementations.

One or more wires (not shown) may be provided within receiver 902 and connector portion 404 to electrically connect receiver 902 and sensor electrode 110-1 to circuitry and/or other electronics within BTE component 402.

Figure 10:
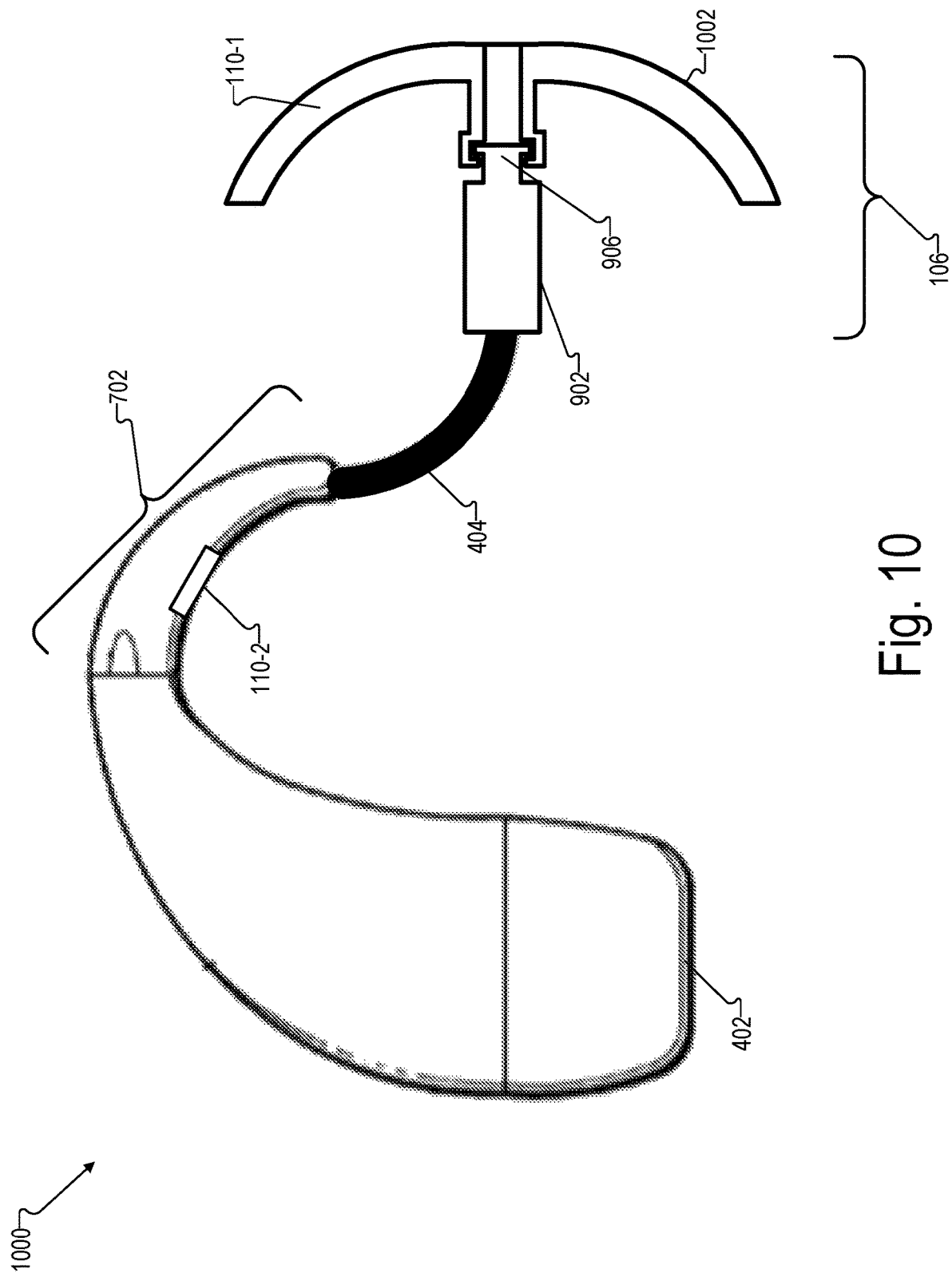

FIG. 10 shows an exemplary configuration 1000 that is similar to configuration 900 shown in FIG. 9 except that FIG. 10 includes a shell 1002 that is formed of a conductive material (e.g., conductive silicone). As such, the entire surface of shell 1002 may be configured to operate as sensor electrode 110-1 while shell 1002 is inserted within the ear canal of the user. In such an example, shell 1002 may electrically connect to conductive spout 906 by way of the contact between shell 1002 and conductive spout 906.

Figure 11:
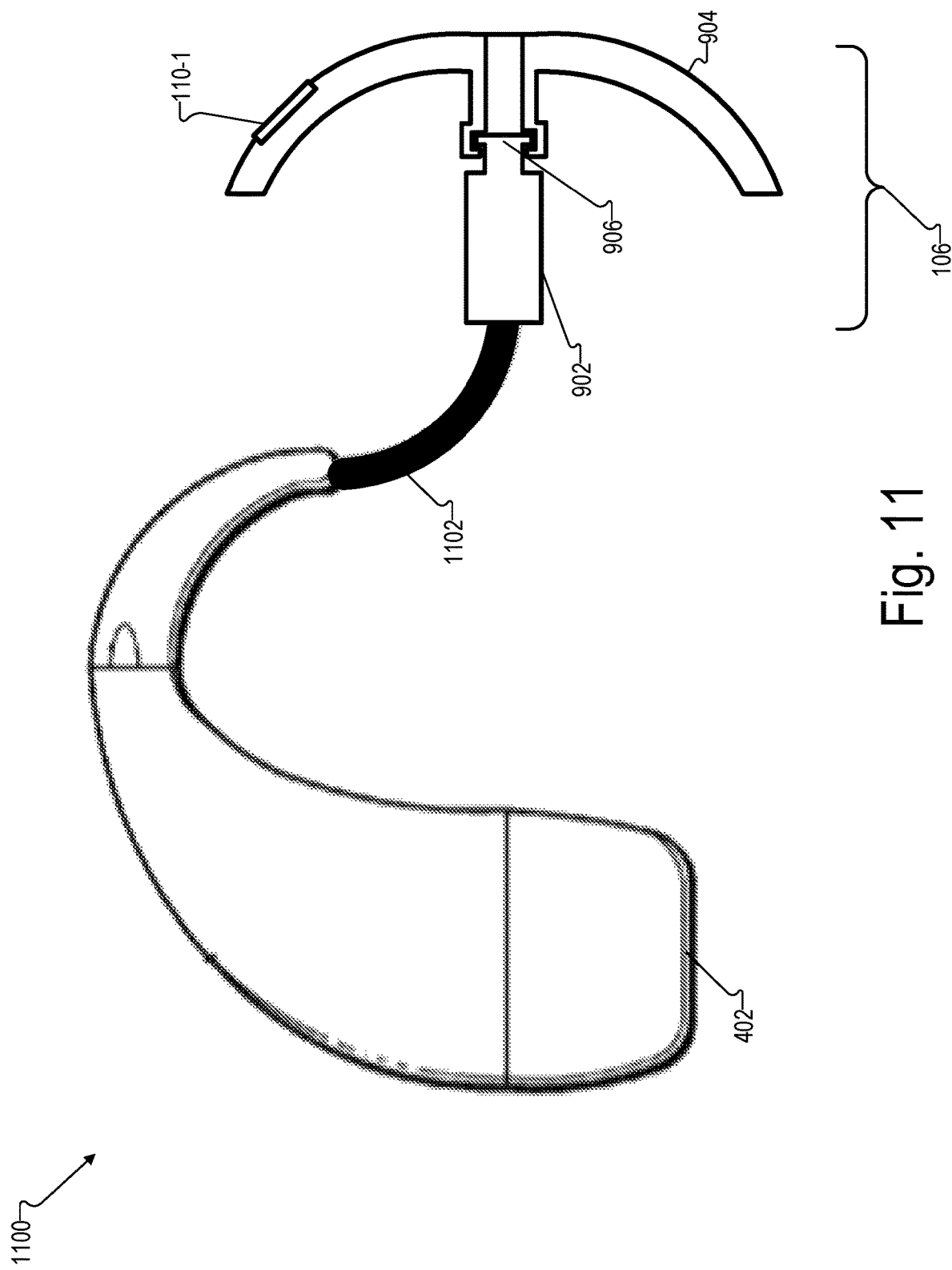

In certain examples, sensor electrode 110-2 may be provided as part of a cable that connects a BTE component to an ITE component. To illustrate, FIG. 11 shows an exemplary configuration 1100 in which a cable 1102 connects BTE component 402 to ITE component 106. Because cable 1102 is configured to contact at least some of the outer ear tissue between BTE component 402 and ITE component 106 when the hearing system is worn by the user, cable 1102 may be used as sensor electrode 110-2 in certain examples. For instance, all or part of cable 1102 may be provided with any suitable conductive outer coating to facilitate cable 1102 operating as sensor electrode 110-2 while hearing system 100 is worn by the user.

Figure 12:
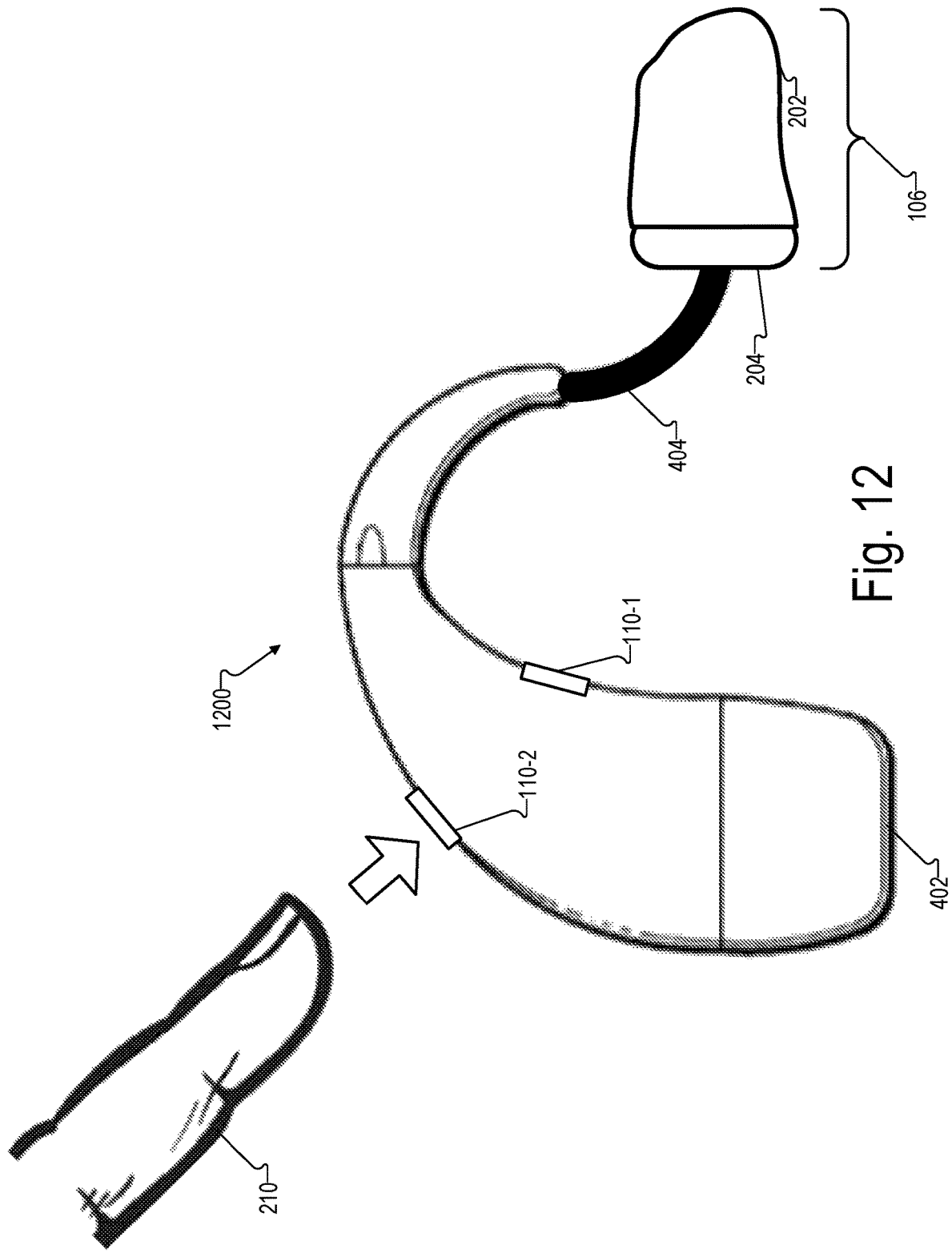

In certain alternative examples, sensor electrodes 110 may only be provided on an outer surface of BTE component 402 and not on other components of hearing system 100 (e.g., not on an outer surface of ITE component 106). To illustrate, FIG. 12 shows an exemplary configuration 1200 in which BTE component 402 includes both sensor electrode 110-1 and sensor electrode 110-2 provided on an outer surface thereof. As shown in FIG. 12, sensor electrode 110-1 is positioned so as to contact a rear portion of the ear of the user while hearing system 100 is worn by the user. On the other hand, sensor electrode 110-2 is configured to contact finger 210 of the user while hearing system 100 is being used to detect the physiological attribute. The relative positions and/or number of sensor electrodes 110-1 and 110-2 shown in FIG. 12 are illustrative of just one possible implementation. It is understood that sensor electrodes 110-1 and 110-2 may be configured differently in other implementations. For example, in addition to sensor electrodes 110-1 and 110-3, additional sensor electrodes 110 may be provided on the hook portion of BTE component 402 and/or a side surface of BTE component 402, such as described herein.

Figure 13:
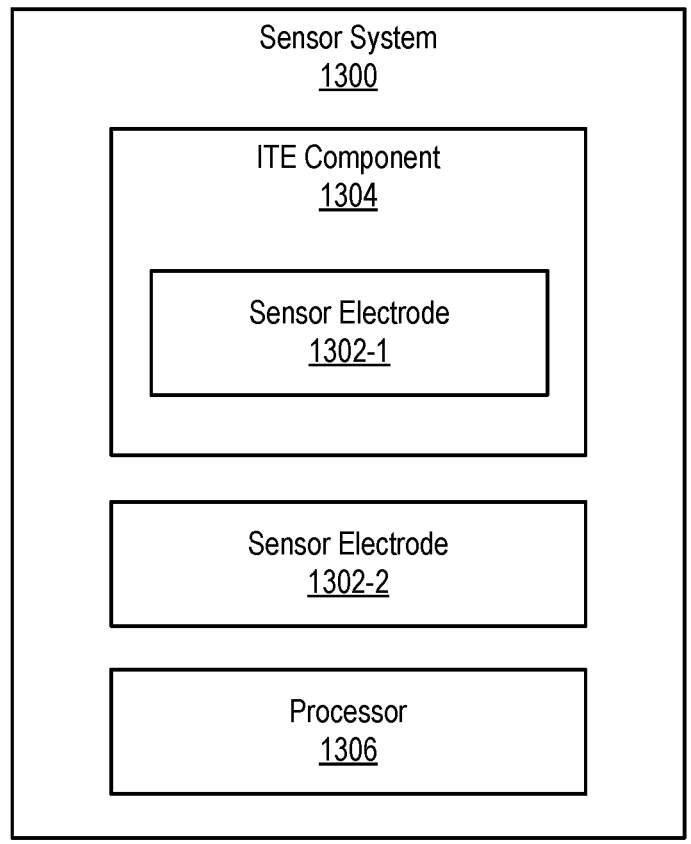
FIG. 13 illustrates an exemplary sensor system according to principles described herein.

FIG. 13 illustrates an exemplary sensor system 1300 that may be implemented in certain examples according to principles described herein. As shown in FIG. 13, sensor system 1300 includes sensor electrodes 1302 (e.g., sensor electrodes 1302-1 and 1302-2) and a processor 1306. Sensor electrode 1302-1 is configured to be provided on a surface an ITE component 1304 in any suitable manner, such as described herein. While a hearing system (e.g., hearing system 100) is worn by the user, sensor electrode 1302-1 is configured to contact outer ear tissue of the user. In addition, while the hearing system is worn by the user, sensor electrode 1302-2 is configured to be located at an entrance to or outside of the ear canal of a user in any suitable manner, such as described herein.

Although only two sensor electrodes 1302 are shown in FIG. 13, it is understood that sensor system 1300 may have additional sensor electrodes in certain implementations. For example, there may be two or more sensor electrodes 1302 provided at different locations on the surface of ITE component 1304 in certain implementations.

Processor 1306 may include or be implemented by hardware and/or software components (e.g., processors, memories, communication interfaces, instructions stored in memory for execution by the processors, etc.). Processor 1306 is configured to control operation of sensor electrodes 1302-1 and 1302-2 to detect one or more physiological attributes of the user while the hearing system is worn by the user. Processor 1306 may control operation of sensor electrodes 1302 an any suitable manner, such as described herein (e.g., similar to processor 104).

Figure 14:
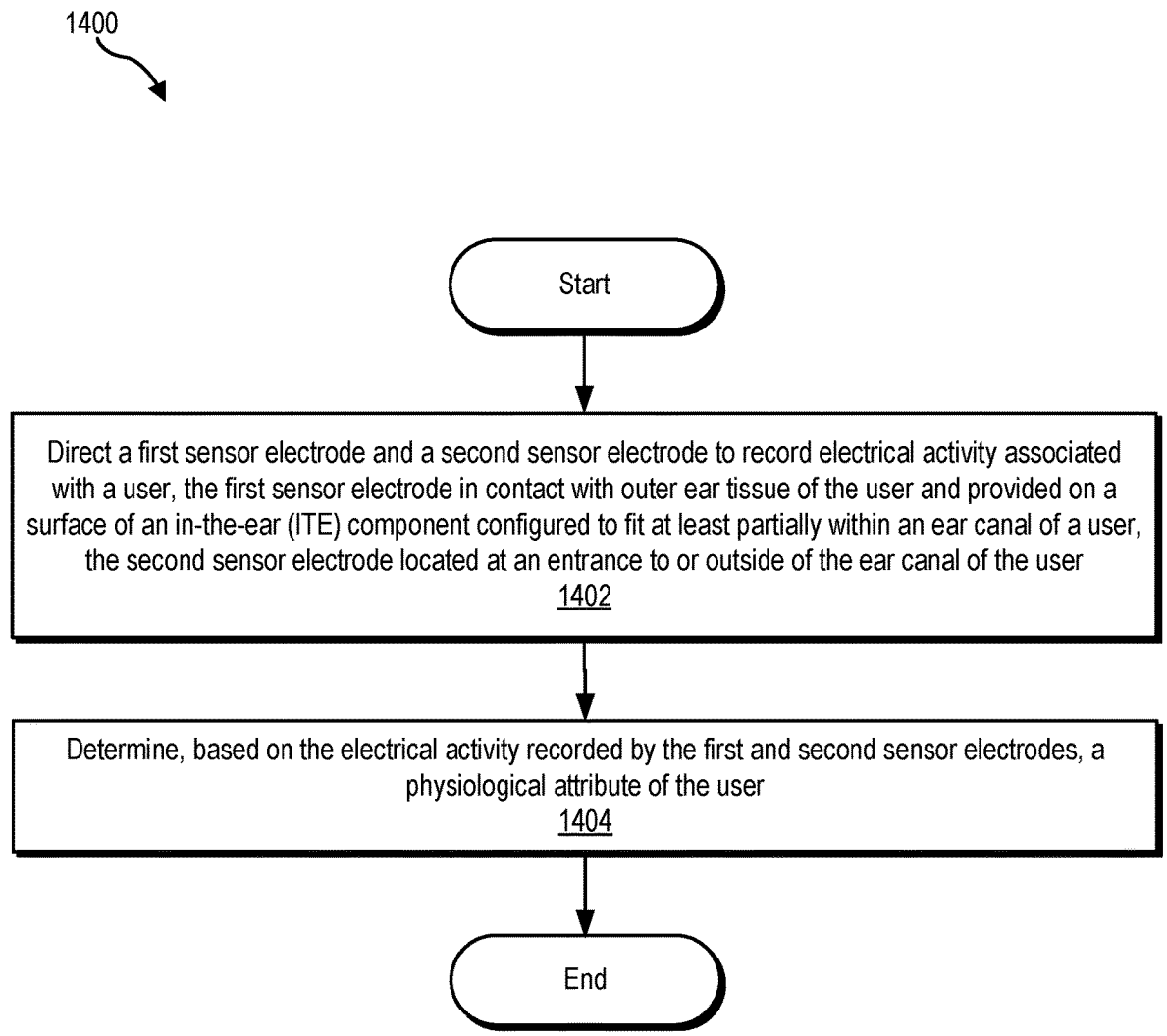
FIG. 14 illustrates an exemplary method for detecting a physiological attribute of a user according to principles described herein.

FIG. 14 illustrates an exemplary method for detecting a physiological attribute of a user according to principles described herein. While FIG. 14 illustrates exemplary operations according to one embodiment, other embodiments may omit, add to, reorder, and/or modify any of the operations shown in FIG. 14. One or more of the operations shown in FIG. 14 may be performed by processor 104, processor 1306, and/or any implementation thereof.

In operation 1402, a processor (e.g., processor 104) directs a first sensor electrode and a second sensor electrode to record electrical activity associated with a user. The first sensor electrode is configured to be in contact with outer ear tissue of the user and is provided on a surface of an ITE component configured to fit at least partially within an ear canal of a user. The second sensor electrode on the other hand is configured to be located at an entrance to or outside of the ear canal of the user. Operation 1402 may be performed in any of the ways described herein.

In operation 1404, the processor determines, based on the electrical activity recorded by the first and second sensor electrodes, a physiological attribute of the user. For example, the processor may utilize the recorded electrical activity in any suitable manner to take an EEG measurement to determine brain activity of the user. Alternatively, the processor may utilize the recorded electrical activity in any suitable manner to take an ECG measurement to determine a heartbeat attribute of the user. Operation 1404 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A hearing system configured to assist a user in hearing, the hearing system comprising:
    an in-the-ear (ITE) component configured to fit at least partially within an ear canal of the user while the hearing system is worn by the user;
    a behind-the-ear (BTE) component that is communicatively coupled to the ITE component;
    a first sensor electrode provided on a surface of the ITE component and configured to contact, while the hearing system is worn by the user, outer ear tissue of the user; and
    a second sensor electrode configured to be located, while the hearing system is worn by the user, at an entrance to or outside of the ear canal of the user,
    wherein:
        the first sensor electrode and the second sensor electrode are configured to be used to detect a physiological attribute of the user while the hearing system is worn by the user;
        the BTE component includes a hook portion configured to contact an upper portion of an ear of the user while the BTE component is worn behind the ear of the user; and
        the second sensor electrode is provided on an outer surface of the hook portion of the BTE component and is configured to contact the outer ear tissue of the user at a top portion of the ear when the BTE component is worn by the user.

2. The hearing system of claim 1, wherein:
    the ITE component comprises:
        a shell that is configured to fit at least partially within the ear canal of the user; and
        a faceplate configured to fit within an opening provided in the shell and face out of the ear canal of the user when the shell is inserted into the ear canal of the user; and
    the first sensor electrode is provided on an outer surface of the shell and is configured to contact a wall of the ear canal when the ITE component is inserted within the ear canal of the user.

3. The hearing system of claim 2, wherein the shell is made from a conductive material such that an entire outer surface of the shell implements the first sensor electrode.

4. The hearing system of claim 1, wherein:
    the ITE component includes a retention member that is configured to be positioned within a concha of an ear of the user when the ITE component is worn by the user, the retention member configured to retain the ITE component at least partially within the ear canal of the user; and the first sensor electrode is provided on the retention member and is configured to contact the concha when the ITE component is worn by the user.

5. The hearing system of claim 1, wherein:
the ITE component includes a shell that is configured to fit at least partially within the ear canal of the user; and
the first sensor electrode is provided on an outer surface of the shell and is configured to contact a wall of the ear canal when the ITE component is worn by the user.

6. The hearing system of claim 5, wherein the shell is made from a conductive material such that an entire outer surface of the shell implements the first sensor electrode.

7. The hearing system of claim 1, wherein the physiological attribute comprises at least one of brain activity indicated in an electroencephalogram (EEG) measurement and a heartbeat attribute indicated in an electrocardiogram (ECG) measurement.

8. The hearing system of claim 1, wherein the hook portion is formed of a conductive material such that an entire outer surface of the hook portion implements the second sensor electrode.

9. A sensor system for use with an in-the-ear (ITE) component and a behind-the-ear (BTE) component of a hearing system configured to assist a user in hearing, the sensor system comprising:
a first sensor electrode provided on a surface of the ITE component and configured to contact, while the hearing system is worn by the user, outer ear tissue of the user;
a second sensor electrode that is provided on an outer surface of a hook portion of the BTE component and that is configured to contact the outer ear tissue of the user at a top portion of an ear of the user when the BTE component is worn by the user; and
a processor configured to control operation of the first sensor electrode and the second sensor electrode that are configured to be used to detect a physiological attribute of the user while the hearing system is worn by the user.

10. The sensor system of claim 9, wherein the physiological attribute comprises at least one of brain activity indicated in an electroencephalogram (EEG) measurement and a heartbeat attribute indicated in an electrocardiogram (ECG) measurement.

11. The sensor system of claim 9, wherein:
the ITE component comprises a shell that is configured to fit at least partially within an ear canal of the user; and
the shell is made from a conductive material such that an entire outer surface of the shell implements the first sensor electrode.

12. The sensor system of claim 9, wherein the hook portion is formed of a conductive material such that an entire outer surface of the hook portion implements the second sensor electrode.

13. A method comprising:
directing, by a processor of a hearing system configured to assist a user in hearing, a first sensor electrode and a second sensor electrode to record electrical activity associated with the user, the first sensor electrode in contact with outer ear tissue of the user and provided on a surface of an in-the-ear (ITE) component configured to fit at least partially within an ear canal of a user, the second sensor electrode is provided on an outer surface of a hook portion of a behind-the-ear (BTE) component and is configured to contact the outer ear tissue of the user at a top portion of an ear of the user when the BTE component is worn by the user; and
determining, by the processor of the hearing system based on the electrical activity recorded by the first and second sensor electrodes, a physiological attribute of the user.

14. The method of claim 13, wherein:
the ITE component comprises a shell that is configured to fit at least partially within the ear canal of the user; and
the shell is made from a conductive material such that an entire outer surface of the shell implements the first sensor electrode.

15. The method of claim 13, wherein the hook portion is formed of a conductive material such that an entire outer surface of the hook portion implements the second sensor electrode.

* * * * *